United States Patent [19]

Disch et al.

[11] Patent Number: 5,438,986
[45] Date of Patent: Aug. 8, 1995

[54] OPTICAL SENSOR

[75] Inventors: Daniel Disch, Beaver Dam, Wis.;
Christopher G. Chin, Granada Hills, Calif.; Josef K. S. Tan, Waukesha, Wis.

[73] Assignee: Criticare Systems, Inc., Waukesha, Wis.

[21] Appl. No.: 166,761

[22] Filed: Dec. 14, 1993

[51] Int. Cl.6 .................................. A61B 5/00
[52] U.S. Cl. ......................... 128/633; 128/666
[58] Field of Search ....................... 128/632–633, 128/637, 664–667; 356/39–41

[56] References Cited

U.S. PATENT DOCUMENTS

| | | | |
|---|---|---|---|
| 3,152,587 | 10/1964 | Ullrich et al. | 128/633 |
| 4,685,464 | 8/1987 | Goldberger et al. | 128/664 X |
| 5,168,876 | 12/1992 | Quedens et al. | 128/642 |
| 5,170,786 | 12/1992 | Thomas et al. | 128/665 X |
| 5,193,542 | 3/1993 | Missanelli et al. | 128/633 |
| 5,209,230 | 5/1993 | Swedlow et al. | 128/633 |
| 5,247,931 | 9/1993 | Norwood | 128/665 X |
| 5,279,295 | 1/1994 | Martens et al. | 128/666 X |
| 5,313,940 | 5/1994 | Fuse et al. | 128/664 X |

Primary Examiner—Angela D. Sykes
Attorney, Agent, or Firm—Reinhart, Boerner, Van Deuren, Norris & Rieselbach

[57] ABSTRACT

An optical sensor, for positioning and holding an optical source and optical detector on opposite sides of a patient's finger or other extremity includes a clothespin-like housing having opposed housing members. The optical source and optical detector are embedded, respectively, in separate, opposed contact pads. The contact pads are mounted on the opposed housing members. A detent mechanism and a carrier associated with each of the housing members and contact pads allows the contact pads to be detached from the housing for cleaning or repair. A pivot mechanism that permits limited lateral as well as rotational movement of the housing members relative to each other allows the sensor to accommodate fingers of varying sizes.

12 Claims, 2 Drawing Sheets

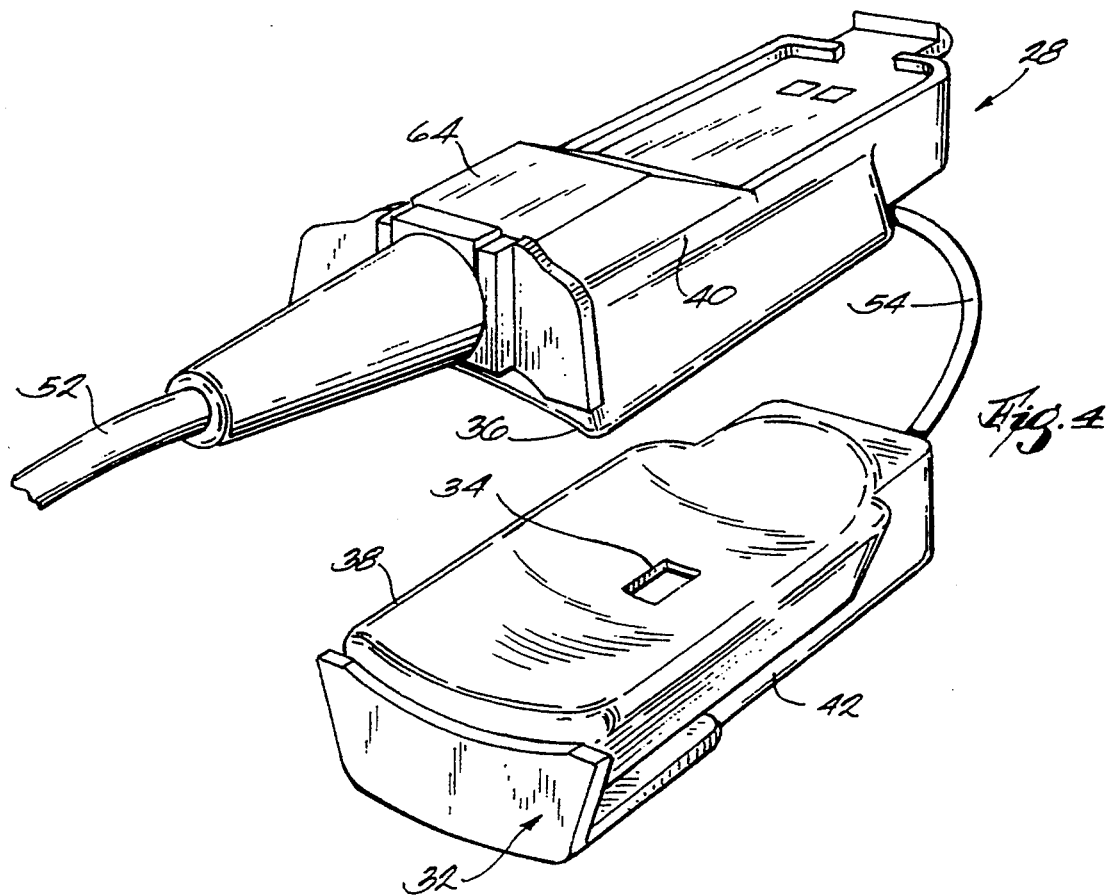

OPTICAL SENSOR

BACKGROUND OF THE INVENTION

This invention relates generally to sensors for sensing physiological functions in a human being and, more particularly, to a clip for positioning and holding an optical sensor adjacent a finger or other body extremity.

Various non-invasive techniques have been developed for sensing physiological functions in a human medical patient. Such non-invasive techniques have the advantage of avoiding physical penetration of the skin. This substantially reduces the risks of infection, trauma and electrical shock and minimizes patient discomfort.

One well known technique for non-invasively sensing physiological functions involves passing infrared or visible light through a portion of a patient's body. By measuring the relative absorption at various wavelengths, information regarding the patient's physiological functions can be derived. Such "optical sensing" is particularly useful in pulse oximetry wherein the instantaneous relative oxygenation of a patient's arterial blood is determined by passing light through a blood-perfused portion of the patient's body (e.g., the finger) and instantaneously measuring the relative absorption at one or more selected wavelengths. Typically, one or more light sources (e.g., light emitting diodes or "LED's") are positioned on one side of the finger, and one or more optical detectors (e.g., photodiodes) are located on the opposite side. A clip device holds both the sources and detectors in their respective, proper positions.

Because it is sometimes necessary to monitor a physiological function for hours, days or even weeks at a time, much consideration must be given to the means by which optical sensing devices are attached or coupled to the patient. On the one hand, a firm means of attachment is desirable in order to ensure continual and reliable monitoring. On the other hand, a too firm means of attachment can cause considerable discomfort, particularly if long term monitoring is involved. Consideration, therefore, must be given to reliability and performance consistent with patient comfort.

Still further consideration should be given to the avoidance of infection and disease transfer. Although non-invasive monitors do not, as a rule, physically enter a patient's body or bloodstream, cleanliness is nevertheless recognized as essential in preventing the spread of disease. Although single-use, disposable devices are one well known way of ensuring sterility and avoiding disease transfer, the disposal of medical waste material is a growing problem, and the costs and waste associated with discarding complex, sophisticated devices after only a single use are becoming increasingly difficult to justify. Preferred devices are those that can be economically manufactured and easily cleaned for multiple use.

One known clip for mounting an optical sensor on a patient's finger is shown in U.S. Pat. No. 4,685,464. In such a clip, a pair of deformable pads, on which are mounted, respectively, a light source and a light detector, in turn are mounted on and adhered to the opposed faces of a rigid, hinged, clothespin-like housing. Although effective, the permanently affixed pads make effective cleaning somewhat difficult and inefficient.

SUMMARY OF THE INVENTION

The invention provides a non-invasive optical sensor comprising a hinged clothespin-like housing having a pair of opposed faces. The sensor includes a first contact pad having an optical source associated therewith and a second contact pad having an optical detector associated therewith. The optical sensor further includes releasable structure for securing the first and second optical pads to the opposed faces of the housing. The first and second contact pads, and the optical source and optical sensor associated therewith, are thereby readily separable from the housing for cleaning or replacement.

In one embodiment, the sensor includes a first detachable carrier engageable with one of the opposed faces of the housing and further includes a second detachable carder engageable with the other of the opposed faces of the housing.

In one embodiment, detents are provided in the housing for retaining the detachable carriers, and push button release mechanisms are provided for releasing the detents to disengage the carriers from the housing.

In one embodiment, the first and second contact pads are mounted, respectively, on the first and second detachable carriers.

In one embodiment, the optical source and the optical sensor are embedded, respectively, within the first and second contact pads.

In one embodiment, the first and second contact pads are shaped to conform to a patient's finger.

In one embodiment, at least one of the first and second contact pads is formed of non-deformable material.

In one embodiment, the housing and the carrier are formed of a molded rigid plastic.

In one embodiment, the contact pad formed of the non-deformable material is coated with a friction enhancing material.

In one embodiment, the housing includes a pair of housing members joined to each other for rotational movement around a pivot axis and for limited lateral movement toward or away from each other at the pivot axis so that the distance between the housing members can be varied over a limited range without changing the angular orientation of the housing member relative to each other to permit use of the housing on fingers of widely varying sizes.

It is an object of the present invention to provide a new and improved sensor for non-invasive optical sensing of physiological functions.

It is a further object of the present invention to provide an optical sensor that can be readily disassembled for easy cleaning and repair.

It is a further object of the present invention to provide a sensor that is effective in maintaining the optical sensing components in a preferred orientation relative to a patient's body while avoiding undue patient discomfort.

It is a further object of the present invention to provide an optical sensor that can be economically manufactured from molded plastic components.

BRIEF DESCRIPTION OF THE DRAWING

The features of the present invention that are believed to be novel are set forth with particularity in the appended claims. The invention, together with the further objects and advantages thereof, may best be understood by reference to the following description taken in conjunction with the accompanying drawings, wherein like reference numerals identify like elements, and wherein:

FIG. 4 is a perspective view of a contact pad assembly constructed in accordance with one aspect of the invention.

FIG. 5 is a cross-sectional view of the optical sensor shown in FIG. 1 taken along line 5—5 thereof.

DESCRIPTION OF THE PREFERRED EMBODIMENT

Figure 1:
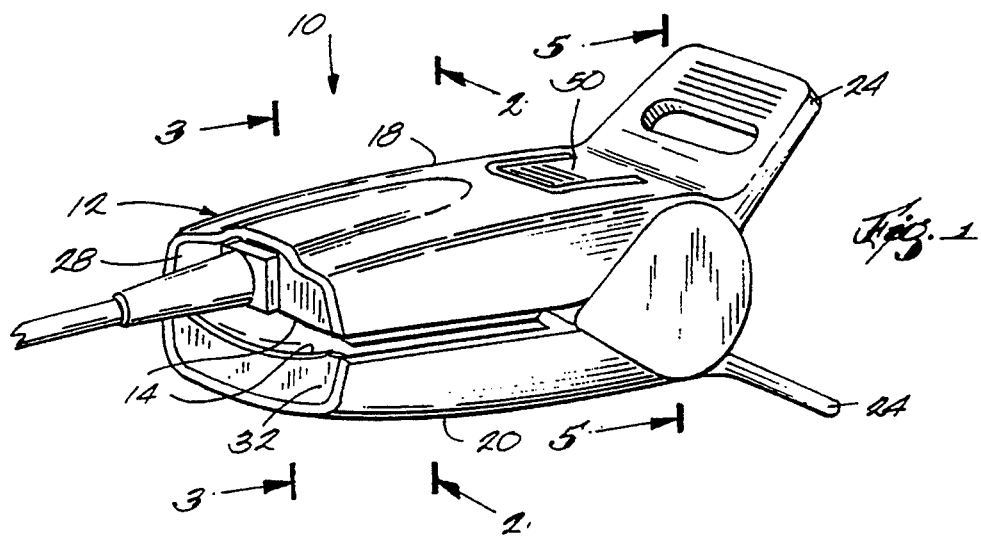
FIG. 1 is a perspective view of an optical sensor constructed in accordance with various features of the invention.

Referring to the figures and, in particular, to FIG. 1, an optical sensor 10 embodying various features of the invention comprises clothespin-like structure adapted to engage an extremity of a patient's body. In the illustrated embodiment, the sensing device 10 is intended for use in pulse oximetry measurements and is adapted to engage a patient's finger or toe.

The sensor 10 includes a hinged, clothespin-like housing 12 having a pair of opposed faces 14 for grasping the patient's finger 16 therebetween. The housing comprises a pair of upper and lower housing members 18, 20 joined to each other for rotational movement around a pivot axis 22. A pair of flanges 24 extending from the rear ends of the housing members 18, 20 can be squeezed together to open the opposed faces 14 and thereby admit the patient's finger 16. A torsion spring 26 coupled to the housing members 18, 20 biases the opposed faces 14 toward each other to help retain the optical sensor 10 in place on the patient's finger 16.

In accordance with one aspect of the invention, the housing members 18, 20 are joined to each other not only for rotational movement around the pivot axis 22 but also for limited lateral movement toward or away from each other at the pivot axis 22 so that the distance between the housing members 18, 20 can be varied over a limited range without substantially changing the angular orientation of the housing members 18, 20 relative to each other. This helps keep the opposed faces 14 of the housing members 18, 20 more or less parallel to each other regardless of whether the patient's finger 16 is relatively thick or thin.

The optical sensor 10 further includes a first contact pad assembly 28 having an optical source 30 associated therewith and a second contact pad assembly 32 having an optical detector 34 associated therewith. The first contact pad assembly 28 is mounted on the upper housing member 18 and the second contact pad assembly 32 is mounted on the lower housing member 20 opposite the first contact pad assembly 28. The optical source 30 and the optical detector 34 are located so as to be opposed to each other.

Figure 3:
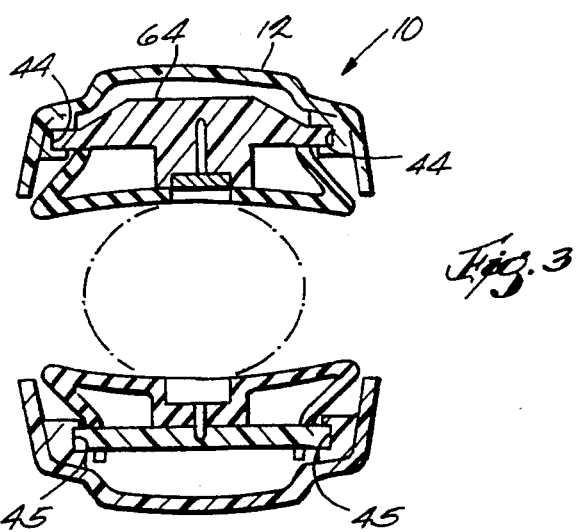
FIG. 3 is a cross-sectional view of the optical sensor shown in FIG. 1 taken along line 3—3 thereof.

In accordance with another aspect of the invention, and to facilitate cleaning or repair of the optical sensor 10, means are provided for releasably securing the first and second contact pad assemblies 28, 32 to the opposed faces of the housing 12. In the illustrated embodiment, the first and second contact pads 36, 38 are mounted on respective first and second detachable carders 40, 42 engageable with the housing members 18, 20. As best seen in FIG. 3, the interiors of the upper and lower housing members 18, 20 are provided with respective pairs of opposed, parallel slots 44, 45 that slideably receive the outer side edges of the carders 40, 42. Detents are provided for securing the carders 40, 42 within the upper and lower housing members 18, 20 when the carders 40, 42 are fully received therein. In the illustrated embodiment, a displaceable tab or hook 46 at the forward end of each carrier 40, 42 engages a complementary tab 48 in the housing member 18, 20. User-depressable means are provided for selectively disengaging the detents securing the first and second carders 40, 42. In the illustrated embodiment, inwardly depressable tabs 50 are formed in the first and second housing members 18, 20 immediately forwardly of the pivot axis 22. In the illustrated embodiment, each depressable tab 50 is defined by a U-shaped slot formed in each of the upper and lower housing members 18, 20. The forward end of each tab 50 includes an inwardly extending portion that, when the tab is depressed, engages the forward end of the hook 46 to disengage it from the tab 48 and thereby permit withdrawal of the carders 40, 42.

As previously noted, the first and second contact pad assemblies 28, 32, and the optical source 30 and optical detector 34 associated therewith, can be removed from the housing 12 to facilitate cleaning and/or repair or replacement of the pads or the housing. As best seen in FIG. 4, an electrical cable 52 that interconnects the optical sensor 10 with an electronic monitoring device is coupled to the optical source 30 of the first contact pad assembly 20 and a second electrical cable 54 interconnects the first electrical cable 52 with the optical detector 34 of the second contact pad assembly 38. Accordingly, the first and second cables 52, 54 and the first and second contact pad assemblies 28, 32, along with the optical source 30 and optical detector 34 associated therewith, can be handled as a single unit when it is removed from the housing 12. To remove the contact pad assemblies from the housing, the depressable tabs 50 of the upper and lower housing members 18, 20 are squeezed inwardly between the fingers while the first and second contact pad assemblies 28, 32 are pulled from the housing 12. To install the contact pad assemblies 28, 32, the assemblies are inserted into their respective housings 18, 20 making sure that the side edges of the carriers 40, 42 are received within their respective slots 44, 45. The pad assemblies are pressed inwardly until the detent hooks 46 engage their respective tabs 48. Preferably, the forward edges of the detent hooks 46 are beveled as shown to deflect the hooks 46 into place as the contact pad assemblies 28, 32 are inserted.

Preferably, the contact pads 36, 38 conform generally to the shape of the finger 16 as shown. The housing members 18, 20 and the carriers 40, 42 are preferably formed of a rigid, durable, injection molded plastic such as acrylonitrile butadiene styrene (ABS) or ABS/polycarbonate. One of the contact pads, e.g., the upper contact pad 36 can be formed of silicone rubber and can be made hollow to enable it to conform to the finger more readily. The opposite contact pad 38 is preferably formed of a rigid, durable, non-deformable plastic such as ABS or rigid PVC, and is preferably of solid construction. To avoid slippage and improve patient feel, a friction enhancing material can be applied. For example, a thin layer of silicone rubber, preferably bless than 0.015 inches thick, can be included on the upper face of the rigid, non-deformable pad 38. Alternatively, the rigid pad 38 can be highly polished to enhance friction. The optical source 30 and the optical detector 34 are each preferably embedded within their respective contact pads 36, 38. The contact pads 36, 38 are preferably securely adhered to the respective carriers 40, 42 by a suitable adhesive, such as a solvent welding agent (e.g., methylene chloride) or room temperature vulcanizing silicone rubber with an appropriate primer.

Figure 2:
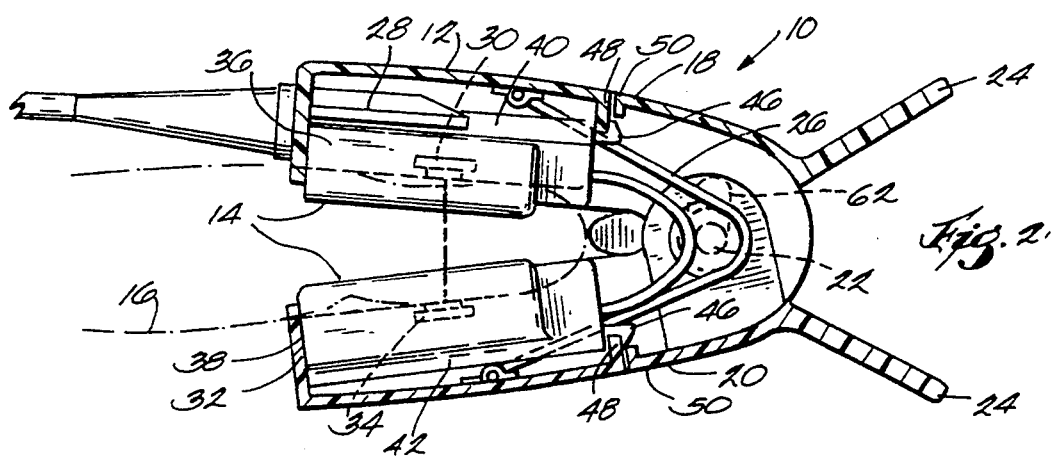
FIG. 2 is a cross-sectional view of the optical sensor shown in FIG. 1 taken along line 2—2 thereof.

As best seen in FIGS. 2 and 5, the limited lateral movement permitted between the joined housing members 18, 20 is provided by means of a pin and slot arrangement included in the upper and lower housings 18, 20. Referring to FIG. 5, the lower housing member 20 includes, at each side, an upwardly projecting tab 56 having an outwardly projecting pin 58 formed thereon. The upper housing member 18 includes, at each side, a downwardly projecting tab 60 having an elongated slot 62 (FIG. 2) formed therein. The pin 58 of the lower housing member 20 is received within the slot 62 of the upper housing member 18 and generally provides for pivoting movement between the housing members 18, 20. Ordinarily, and as seen in FIG. 5, the bias of the torsion spring 26 pulls the pin 58 toward the upper end of the slot 62 thereby minimizing the distance between the upper and lower housing members 18, 20. When the sensor 10 is in place on the finger 16, the pin 58 can move toward the lower end of the slot 62 as needed to maintain the desired orientation of the sensor 10 on the finger 16.

Preferably, the contact pad assemblies 28, 32 and housing members 15, 20 are keyed so that the upper contact assembly 28, for example, will not fit in the lower housing member 20. This prevents improper installation of the pad assemblies and assures proper assembly of the optical sensor. In the illustrated embodiment, the width of the carders 40, 42 and their respective slots 44, 45 are different so as to prevent installation of the upper assembly 28 into the lower housing member 20 or the lower assembly 32 into the upper housing member 18.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A non-invasive optical sensor comprising:
   a hinged clothespin-like housing having a pair of opposed faces;
   a first contact pad having an optical source associated therewith;
   a second contact pad having an optical detector associated therewith; and
   releasable means for securing said first and second optical pads to said opposed faces of said housing;
   said first and second contact pads and said optical source and said optical sensor associated therewith thereby being readily separable from said housing for cleaning or replacement;
   said releasable means including a first detachable carrier engageable with one of said opposed faces and a second detachable carrier engageable with the other of said opposed faces;
   said first and second detachable carriers engaging respective detents in said housing adjacent said opposed faces;
   said housing further including depressable means for selectively disengaging said first and second carrier from said respective detents.

2. A sensor as defined in claim 1 wherein said first and second contact pads are mounted, respectively, on said first and second detachable carriers.

3. A sensor as defined in claim 2 wherein said optical source and said optical sensor are embedded, respectively, within said first and second contact pads.

4. A sensor as defined in claim 3 wherein said first and second contact pads are shaped to conform to an extremity of the patient's body.

5. A sensor as defined in claim 4 wherein at least one of said first and second contact pads is formed of a non-deformable material.

6. A sensor as defined in claim 5 wherein said housing and said carrier are formed of a molded rigid plastic.

7. A sensor as defined in claim 6 wherein said contact pad formed of said non-deformable material is coated with a friction enhancing material.

8. A sensor as defined in claim 7 wherein said friction enhancing material a layer of silicone rubber less than substantially 0.015 inches thick.

9. A sensor as defined in claim 6 wherein said contact pad formed of said non-deformable material is polished to enhance friction between said non-deformable material and the body extremity.

10. A sensor as defined in claim 9 wherein the body extremity is a finger and said first and second contact pads are adapted to conform to the finger.

11. A sensor as defined in claim 1 wherein said housing comprises a pair of housing members joined to each other for rotational movement around a pivot axis and for limited lateral movement toward or away from each other at said pivot axis so that the distance between said housing members can be varied over a limited range without changing the angular orientation of said housing members relative to each other.

12. A sensor as defined in claim 1 wherein said sensor further includes keying means for ensuring that said first and second contact pads can be secured to said housing in only one unique orientation.

* * * * *